United States Patent [19]

Klocke et al.

[11] Patent Number: 5,001,149

[45] Date of Patent: Mar. 19, 1991

[54] AZADIRACHTIN DERIVATIVE INSECTICIDES

[75] Inventors: James A. Klocke; Ronald B. Yamasaki, both of Salt Lake City, Utah

[73] Assignee: NPI, Salt Lake City, Utah

[21] Appl. No.: 21,807

[22] Filed: Mar. 4, 1987

[51] Int. Cl.$^5$ ............................................. A01N 43/20
[52] U.S. Cl. .................................................. 514/468
[58] Field of Search ................. 514/453, 468; 549/456, 549/472

[56] References Cited

U.S. PATENT DOCUMENTS 4,556,562 12/1985 Larson ............................... 424/195.1

OTHER PUBLICATIONS

Kubo et al., "Insect Ecdysis Inhibitors", in Natural Resistance of Plants to Pests, pp. 206–219, ACS Sympsosium Series 296 (1986).
Morgan, "Strategy in the Isolation of Insect Control Substances from Plants," Proc. 1st Int. Neem Conf., pp. 43–52 (Rottach–Egerm 1980), (Schmutterer et al., Eds. 1982).
Butterworth et. at., J. Chem Soc. (Chem. Commun) pp. 23–24 (1968).
Qadri, et al., Indian J. Exp. Biol. 16: 1141–1143 (1978).
Sieber, et al., J. Insect Physiol. 29: 523–527 (1983).
Kubo et al., Agric. Biol. Chem 46 (7): 1951–1953 (1982).
Litchfield et al., J. Pharm & Exp Therapeutics 96: 99–113 (1949).
Yamasaki et al., J. Chromatog. 356: 220–226 (1986).
Truman et al., Nature 291: 70–71 (1981).
Truman, Amer. Zool. 21: 655–661 (1981).
Taylor et al., Abstract No. 177, Intnl. Res. Cong. on Nat. Prod., Chapel Hill, N.C. (Jul. 1985).
Broughton et al., J. Chem. Soc. (Chem. Commun.) 47, (1986).
Bokel et al., J. Chem Soc. (Chem. Commun.) 523 (1986).
Kubo et al., "Plant Resistance to Insects", pp. 329–346, ACS Symposium Series 208, (1983).
Lee et al., J. Liq. Chromatog, 10(6): 1151–1163 (1987).

*Primary Examiner*—John W. Rollins
*Attorney, Agent, or Firm*—Lyon & Lyon

[57] ABSTRACT

Derivatives of azadirachtin are described which should facilitate their synthesis and provide greater stability than their naturally-occurring counterpart. The derivative 2′,3′,22,-23-tetraydroanzadirachtin is also described, that derivative retaining full activity and having enhanced stability. Insecticidal and antifeedant compositions including these compounds also described.

12 Claims, 1 Drawing Sheet

AZADIRACHTIN DERIVATIVE INSECTICIDES

FIELD OF THE INVENTION

The field of the invention is insecticides. More specifically, it relates insecticidal and antifeedant derivatives of naturally occurring insect ecdysis inhibitors.

BACKGROUND OF THE INVENTION

A requisite for developmental growth in insects is molting. Molting is the entire process by which an insect's old cuticle is shed. The process of molting is initiated when the insect molting hormone ecdysterone (20-hydroxyecdysone) stimulates the epidermis to retract from the cuticle. This retraction of the epidermis from the cuticle is termed "apolysis". Apolysis is immediately followed by mitotic division of the epidermal cells and their subsequent secretion of a protective procuticle and a gel-like molting fluid.

Following activation of the molting fluid, enzymatic digestion of the old cuticle for resorption and reuse results in a thin (i.e., undigested) remnant of the old cuticle which is subsequently split and cast off by the insect. This remnant of the old cuticle which is eventually split and cast off is called the "exuvia". The casting off of the exuvia is termed "ecdysis". Ecdysis is accomplished by hydrostatic pressure brought about by the swallowing of air or water by the insect and its subsequent performance of muscular activities.

When a new cuticle is synthesized, it is soft and flexible so that the hydrostatic pressures brought about by the insect unfold and expand it. In this way, the new cuticle increases its surface area and the old cuticle is concomitantly cast off.

After ecdysis, expansion of the new cuticle is brought to an end by the onset of "sclerotization". Sclerotization involves the cross-linking of cuticular protein with orthoquinone. The source of the ortho-quinone is tyrosine, whose mobilization is controlled by ecdysterone and a peptide hormone called bursicon.

Thus, the major events of the molting process are apolysis (retraction of the cuticle), cuticular synthesis, ecdysis (casting off of the exuvia), and sclerotization. The complexity of the sequence of the physiological and developmental events occurring in the molting process, and the high degree of hormonal coordination with which the entire process must proceed, render the insect which must molt particularly vulnerable to exogenously applied chemicals.

The present invention deals with derivatives of a naturally-occurring chemical which inhibits or prevents ecdysis.

As noted, the actual shedding of the cuticle is termed ecdysis. Ecdysis is triggered by a neurosecretory peptide called "eclosion hormone" which acts on the central nervous system to elicit the ecdysial motor programmes. Truman, J. W., et al., *Nature (London)* 291:70-1 (1981). The release of eclosion hormone is in turn regulated by the molting hormone ecdysterone. Truman, J. W., *Amer. Zool.* 21:655-61 (1981). The inhibition of ecdysis, which can occur through a disruption of the normal titres of ecdysterone or eclosion hormone, is easily observed as a gross morphological event in which the "old" cuticle remains enveloping the insect in the pharate condition. The abnormal pharate condition prevents the feeding and locomotion of the affected insect and eventually results in death. A number of ecdysis inhibitors, including ecdysterone, JH (Juvenile Hormone), and phenylurea compounds are known and have previously been discussed. Kubo & Klocke, "Insect Ecdysis Inhibitors," in "Natural Resistance of Plants to Pests (Roles of Allelochemicals)", ACS Symposium Series 296 (Green and Hedin eds.) Chapter 17, pages 206-219 (American Chemical Society 1986). This and all other publications referred to herein are incorporated by reference.

A natural plant compound which is known to inhibit ecdysis in insects, by some unknown mechanism, is azadirachtin. Morgan, "Strategy in the Isolation of Insect Control Substances From Plants," Proc. First Inter. Neem Conf. pages 43-52 (Rottach-Egern 1980). Azadirachtin is a tetranortriterpenoid of the limonoid type isolated from the seeds of the neem tree (*Azadirachta indica*) and the fruits of the chinaberry tree (*Melia azedarach*). Butterworth, J. H., et al., *J. Chem. Soc.*, Chem. Commun. 23-4 (1968). Although the skeletal structure and stereochemistry of azadirachtin have not been totally resolved, Taylor, R. B., et al., Abstract No. 177, Int'l Research Cong. on Natural Products, Chapel Hill, N.C. (July 1985), the potent ecdysis inhibitory activity of this compound is well-known. Qadri, S. S. H., et al., *Indian J. Exp. Biol.* 16:1141-3 (1978); Sieber, K. P., et al., *J. Insect Physiol.* 29:523-7 (1983); Kubo, I., et al., *Agric. Biol. Chem.* 46:1951-53 (1982).

Another natural product which was isolated from the neem tree and found to have protein ecdysis inhibitory activity is deacctylazadirachtinol. Although deacetylazadirachtinol was shown in one study to be about 2.5-fold less active than azadirachtin as an insect growth inhibitor, in that same study the two compounds were shown to have the same ecdysis inhibitory activity (Kubo & Klocke, supra).

SUMMARY OF THE INVENTION

Derivatives of azadirachtin are described which should facilitate their synthesis and provide greater stability than their naturally-occurring counterpart. The derivative 2',3',22,23-tetrahydroazadirachtin is also described, that derivative retaining full activity and having enhanced stability. Insecticidal and antifeedant compositions including these compounds are also described.

DETAILED DESCRIPTION OF THE INVENTION

Figure 1:
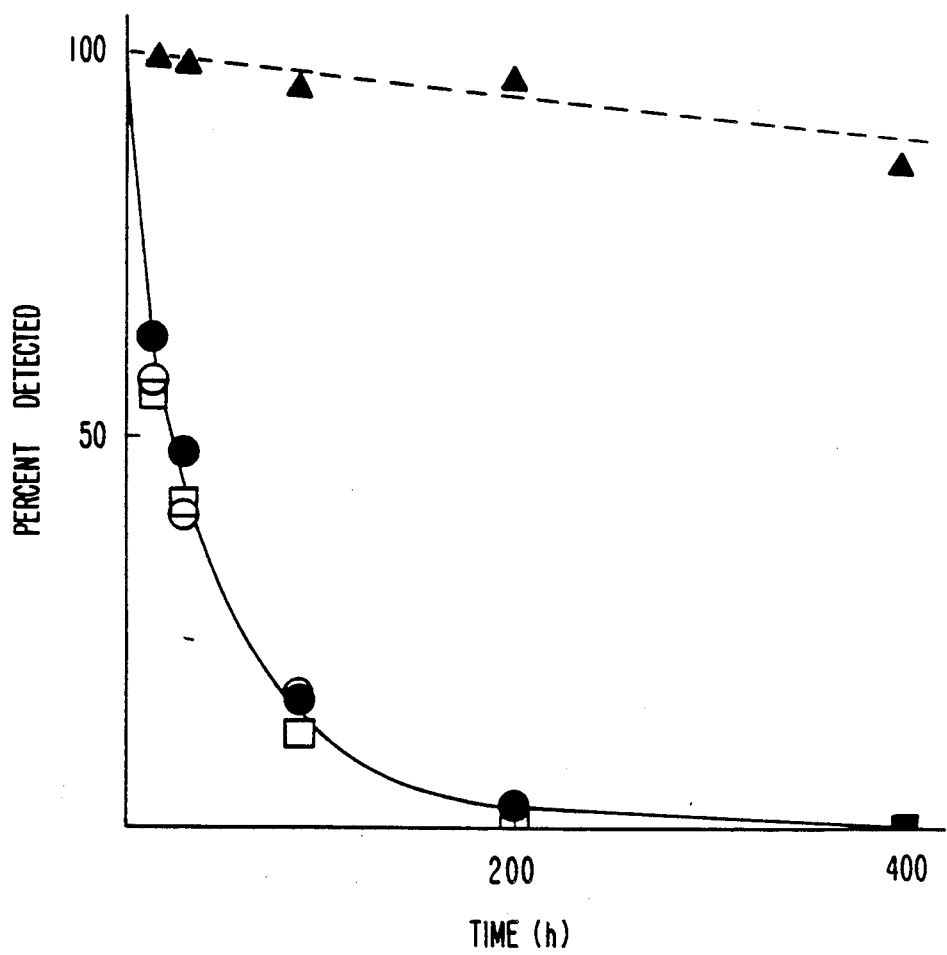

Several derivatives of azadirachtin were prepared and their structures confirmed by infrared and nuclear magnetic resonance spectroscopy.

Referring to the numbered compounds of Table 1, transesterification of azadirachtin (1) with sodium methoxide gave 3-deacetylazadirachtin (2). Heating a solution of azadirachtin (1) and acetic anhydride at reflux gave a monoacetylated product, 13O-acetylazadirachtin (4).

Treatment of azadirachtin (1) with iodomethane and silver (I) oxide gave monomethylated product, most likely 13-O-methylazadirachtin (5), as shown by IR and 'H-NMR spectroscopy.

22,23-dihydroazadirachtin (3) was made by hydrogenation of azadirachtin over platinum (IV) oxide at 5 atm pressure. 2',3',22,23-tetrahydroazadirachtin (8) was made by hydrogenation of azadirachtin over palladium catalyst, which was successful only when using elevated pressures.

The tigloyl group was removed by oxidizing 22,23-dihydroazadirachtin (3) with osmium tetroxide and excess sodium periodate and then hydrolyzing the resulting pyruvate ester with mild aqueous alkali. The product was 1-detigloyl-22,23dihydroazadirachtin (7). When this reaction sequence was repeated using an amount of sodium periodate approximately equimolar with 22,23-dihydroazadirachtin (3), 2',3'-dihydroxy-2',3'22,23-tetrahydroazadirachtin (9) was obtained in about 50% yield.

Heating 22,23-dihydroazadirachtin (3) with dimethyl pyrocarbonate gave a dicarbomethoxylated product, unlike the acetylation reaction where only one hydroxyl group esterified. The structure most consistent with IR and NMR spectra is 13,20-O, O-dicarbomethoxy-22,23-dihydroazadirachtin (6).

The result of the growth inhibitory and lethal activities of azadirachtin and these 8 derivatives are shown in Table 1. Similar to the results of Morgan, E. D., in "Natural pesticides from the Neem tree (*Azadirachta indica* A. Juss), Schmutterer, H., et al., Eds., Proc. First International Neem Conference (Rottach-Egern, 1980), German Agency for Technical Corporation, Eschborn, Germany, 1982, pps. 43-52 (hereinafter "Morgan"), neither deacetylation nor hydrogenation of the carbon-carbon double bond of the dihydrofuran ring moiety of azadirachtin had any significant effect on activity of the compound against *H. virescens*.

Also similar to the structure-activity results of Morgan was the finding that acetylation of the hydroxyl group at position 13 resulted in a slight decrease in the activity of the natural product. More effective in the reduction of activity at this position was methylation. Other derivatives made at the hydroxyl groups at positions 13 and 20 also resulted in diminished activity. For example, derivatization of these hydroxyl groups with trimethylsilyl groups (Morgan) or with dimethylpyrocarbonate to yield the dicarbomethoxy derivatives resulted in decreased activity.

The Table 1 data indicate that the tetrahydro derivative of azadirachtin, 2',3',22,23-tetrahydroazadirachtin, is fully active. Other results described below further demonstrate that this derivative is more stable than the natural product.

TABLE 1

Mortality and growth inhibition in first-instar *Heliothis virescens* larvae fed azadirachtin and eight derivatives in an artificial diet.[a]

| Test Compound | $LC_{50}(ppm)^b$ | $EC_{50}(ppm)^c$ |
|---|---|---|
| 1. azadirachtin | 0.80 (0.46–1.39) | 0.07 (0.05–0.10) |
| 2. 3-deacetylazadirachtin | 0.37 (0.17–0.80) | 0.09 (0.05–0.17) |
| 3. 22,23-dihydroazadirachtin | 0.47 (0.32–0.67) | 0.08 (0.04–0.15) |
| 4. 13-O-acetylazadirachtin | 0.95 (0.59–1.54) | 0.18 (0.08–0.40) |
| 5. 13-O-methylazadirachtin | 25.0 (12.2–51.4) | 5.00 (1.54–16.25) |
| 6. 13,20-O,O-dicarbomethoxy-22,23-dihydroazadirachtin | 90.0 (37.8–214.5) | 29.0 (20.3–41.5) |
| 7. 1-detigloyl-22,23-dihydro-azadirachtin | 2.40 (1.15–5.02) | 0.59 (0.30–1.14) |
| 8. 2',3',22,23-tetrahydro-azadirachtin | 0.30 (0.11–0.80) | 0.08 (0.05–0.13) |
| 9. 2',3'-dihydroxy-2',3',22,23-tetrahydroazadirachtin | 42.0 (32.3–54.6) | 3.80 (1.95–7.41) |

[a] Similar results were obtained against the corn earworm (*Heliothis zea*) and the fall armyworm (*Spodoptera frugiperda*).
[b] $LC_{50}$ values are the concentrations (ppm) causing 50% mortality.
[c] $EC_{50}$ values are the concentrations (PPM) causing 50% growth inhibition.
[d] Numbers in parentheses are the 95% confidence limits determined using the methods of Litchfield and Wilcoxon, J. Pharmacol. Exp. Ther. 96:99–113 (1949).

EXPERIMENTAL

Solvents used for high performance liquid chromatography (HPLC) were of HPLC grade. Other chemicals were of reagent grade or better and were used without further purification unless noted otherwise.

Preparative HPLC was carried out with a Micromeritics Model 750 Solvent Delivery System equiped with a Negretti and Zambra injector, a Micromeritics Model 787 variable wavelength UV/VIS detector, a Hewlett-Packard 3388A integrator/recorder and a Gilson Model 201 fraction collector. Chromatography was accomplished using either a normal phase Alltech Associates silica gel (10 μm particle size) stainless steel column (25×1.0 cm I.D.) protected with an Alltech Associates stainless steel guard column (5.0×0.46 cm I.D.) packed with Alltech Associates pellicular silica gel or a reversed phase Regis Chemical Company octadecylsilyl-silica gel (ODS) (10 μm particle size) stainless steel column (25×1.0 cm I.D.), protected with an Alltech Associates stainless steel guard column (5.0×0.46 cm I.D.) packed with Alltech Associates pellicular ODS. The solvent (vide infra) was eluted at a flow rate of 5.00 ml/min.

Analytical HPLC was performed as described by Yamasaki et al, 1986. All prepared derivatives of azadirachtin were purified to greater than 98% purity. Azadirachtin was isolated and purified from neem seeds by the method of Yamasaki, R. B., et al. *J. Chromatogr.* 356:220–226 (1986) (hereinafter "Yamasaki et al.").

Azadirachtin (30 mg, 0.042 mmol) and 0.5 ml of ethanol was stirred with 20 mg of 5% palladium on alumina at 20° C. under hydrogen (10 atm) for 3 hours. The reaction mixture was then filtered and rotary evaporated in vacuo. The crude product was purified by silica gel preparative HPLC (solvent=2-propanol:n-hexane, 17:83, v/v), followed by ODS preparative HPLC (solvent=methanol:water, 1:1, v/v) to give 2',3',22,23-tetrahydroazadirachtin (18 mg).

Stability of Azadirachtin derivatives was determined as follows:

Azadirachtin and its derivatives listed above (1.0 mg/ml absolute ethanol) were placed individually in capped quartz NMR tubes (5×180 mm) and were irradiated with two UV germicidal lights (GE, G30T8, 200–280 nm, 30 W) 1.8 m from the source at room temperature for up to 400 h. The controls were identical samples protected from exposure to UV radiation by wrapping with aluminum foil. At selected time intervals, aliquots from both the controls (non-irradiated) and irradiated samples were removed for high-performance liquid chromatography (HPLC) analysis (vide infra) and bioassay.

Analytical reversed phase HPLC was performed on a phenyl (5 μm) column run isocratically with acetonitrile-water (3:7) (Yamasaki et al.) Peaks were detected at 214 nm. The irradiated samples were compared with their corresponding non-UV-irradiated controls by measuring the height of the peak eluting at the appropriate $R_t$ for each irradiated compound relative to each one's non-irradiated control. Results are expressed as the percent of the initial sample concentration remaining relative to the control. Each time point was done in at least triplicate fashion.

Individual larvae were injected per os on the first day of the fifth instar with 1.0 μg of one of the either irradiated or non-irradiated compounds dissolved in 1.0 μl of 75% aqueous ethanol. The activity of the non-irradiated compounds is shown in Table 2. Azadirachtin and 2',3',22,23-tetrahydroazadirachtin were equally effective in inhibiting pupation of *H. virescens* larvae (i.e., in reducing the number of larvae that developed into pupae). 3-deacetylazadirachtin and 22,23-dihydroazadirachtin were less effective. However, all four compounds strongly inhibited the development of the larvae to the adult stage. The ability of these compounds to inhibit pupation and the emergence of morphologically normal adults was expressed as the ratio between the percentage of larvae that failed to pupate (Table 3) or to reach the adult stage (Table 4) when injected with irradiated and when injected with the corresponding non-irradiated compounds, multiplied by 100%.

The activity of the irradiated compounds, relative to the activity of the non-irradiated compounds, is shown in Tables 3 and 4. The ability of azadirachtin, 3-deacetylazadirachtin, and 22,23-dihydroazadirachtin to inhibit pupation was not appreciably reduced by up to 90 h of exposure to the UV radiation, but did decline, for all three compounds, after 200 h of exposure. An even greater decline in the ability of these three compounds to inhibit pupation was noted after 400 h of exposure. 2',3',22,23-tetrahydroazadirachtin was most active in inhibiting pupation after 200 h of UV exposure, and although its activity declined after 400 h of exposure, it was still more active than the other test compounds (Table 3).

Similar to the results in Table 2, 90 h of exposure to the UV radiation did not reduce the ability of the four compounds to inhibit the larvae from reaching the adult stage (Table 4). After 200 h of irradiation, the activity of azadirachtin declined slightly and that of 22,23-dihydroazadirachtin more so. The activity of 3-deacetylazadirachtin remained substantially unchanged until 400 h of irradiation. 2',3',22,23-tetrahydroazadirachtin, however, was fully active after 400 h of irradiation.

Using reversed phase HPLC, the relative retention times ($R_t$) were determined, at 214 nm, to be 10.2, 7.5, 9.0, and 9.9 min, for azadirachtin, 3-deacetylazadirachtin, 22,23-dihydroazadirachtin, and 2',3',22,23-tetrahydroazadirachtin, respectively. Thus, azadirachtin, 3-deacetylazadirachtin, and 22,23-dihydroazadirachtin were found to be UV-labile (FIG. 1) and, under the conditions used, the three compounds appeared to be degraded in a first-order reaction (data not shown). Furthermore, all three compounds degraded at essentially the same rate ($T_{\frac{1}{2}}=25$ h). In sharp contrast, 2',3',22,23-tetrahydroazadirachtin exhibited no degradation following 200 h of exposure to UV radiation, and only slight degradation following 400 h of exposure (FIG. 1). HPLC analysis of the non-irradiated compounds showed no change throughout the experiment in the heights of the peaks eluting at the appropriate $R_t$'s.

TABLE 2

|  | Number Larvae | Unsuccessful Larvae-Pupae | Number Pupae | Unsuccessful Pupae-Adult | Number Adults | Number Adults Deformed | % Mortality Prior to Adult Stage |
|---|---|---|---|---|---|---|---|
| Azadirachtin | 149 | 5 | 10 | 0 | 2 | 1 | 98.7 |
| % |  | 3.4 | 6.7 | 0 | 1.3 | 0.7 |  |
| 3-Deacetyl-azadirachtin | 169 | 13 | 56 | 4 | 10 | 10 | 94.1 |
| % |  | 7.7 | 33.1 | 2.4 | 5.9 | 5.9 |  |
| 22,23-Dihydro-azadirachtin | 176 | 13 | 47 | 4 | 6 | 5 | 96.6 |
| % |  | 7.4 | 26.7 | 2.3 | 3.4 | 2.8 |  |
| 2',3',22,23-Tetrahydro azadirachtin | 135 | 6 | 10 | 1 | 0 | 0 | 100 |
| % |  | 4.4 | 7.4 | 0.7 | 0 | 0 |  |

Table 2:
Successful and unsuccessful pupal and adult development of fifth-instar *Heliothis Virescens* larvae injected orally with 1.0 microgram of either azadirachtin, 3-deacetylazadirachtin, 22,23-dihydroazadirachtin, or 2',3',22,23-tetrahydroazadirachtin.

TABLE 3

|  | Azadirachtin | 3-Deacetyl-azadirachtin | 22,23-Dihydro-azadirachtin | 2',3',22,23-Tetra hydroazadirachtin |
|---|---|---|---|---|
| 15 h | 98.6 | 115.2 | 113.1 | 99.4 |
| 30 h | 98.9 | 135.0 | 104.6 | 103.7 |
| 90 h | 85.7 | 139.5 | 100.0 | 99.7 |
| 200 h | 74.2 | 86.8 | 72.7 | 108.0 |
| 400 h | 60.0 | 41.0 | 49.1 | 69.1 |
| N = | 127 | 152 | 150 | 128 |

Table 3:
Relative activity of azadirachtin, 3-deacetylazadirachtin, 22,23-dihydroazadirachtin, and 2',3',22,23-tetrahydroazadirachtin, all of which had been exposed for 15, 30, 90, 200, and 400 hours to UV radiation, inhibiting the pupal development of fifth-instar *Heliothis virescens* larvae. Relative activity is defined as the percentage of larvae injected with each irradiated compound that failed to pupate relative to the percentage injected with its non-irradiated counterpart that failed to pupate, times 100.

TABLE 4

|  | Azadirachtin | 3-Deacetyl-azadirachtin | 22,23-Dihydro-azadirachtin | 2',3',22,23-Tetra hydroazadirachtin |
|---|---|---|---|---|
| 15 h | 101.3 | 103.2 | 103.5 | 100.0 |

TABLE 4-continued

| | Azadirachtin | 3-Deacetyl-azadirachtin | 22,23-Dihydro-azadirachtin | 2',3',22,23-Tetra hydroazadirachtin |
| --- | --- | --- | --- | --- |
| 30 h | 101.3 | 106.3 | 100.1 | 100.0 |
| 90 h | 97.3 | 106.3 | 103.5 | 100.0 |
| 200 h | 89.7 | 96.0 | 69.0 | 100.0 |
| 400 h | 81.1 | 72.3 | 74.5 | 100.0 |
| N = | 127 | 152 | 150 | 128 |

Table 4:
Relative activity of azadirachtin, 3-deacetylazadirachtin, 22,23-dihydroazadirachtin, 2',3',22,23-tetrahydroazadirachtin, all of which had been exposed for 15, 30, 90, 200, and 400 hours to UV radiation, in inhibiting the adult development of fifth-instar *Heliothis virescens* larvae. Relative activity is defined as the percentage of larvae injected with each irradiated compound that failed to reach the adult stage relative to the percentage injected with its non-irradiated counterpart that failed to reach the adult stage, times 100.

That azadirachtin, 3-deacetylazadirachtin, and 22,23-dihydroazadirachtin were UV-labile as indicated using HPLC, may best be explained by the presence in each compound of a tigloyl group. This alpha, beta-unsaturated carbonyl moiety is a strong chromophore and perhaps the major site of chemical degradation since the three compounds that contain it show the same rate of reaction. 2',3',22,23-tetrahydroazadirachtin does not contain a strong chromophore, i.e., the tigloyl group is reduced to a saturated cabonyl system, and it is, hence, not UV-labile.

Apparently, one or more of the UV-degradation products of azadirachtin, 3-deacetylazadirachtin, and 22,23-dihydroazadirachtin were as active as the native molecules. For instance, more than 80% of the three compounds was degraded after 90 h of exposure to UV radiation, yet all three retained full activity. After 400 h of exposure, none of the three compounds remained in their original state, yet all three retained approximately 50% of their activity. In the case of 2',3',22,23-tetrahydroazadirachtin, only after 400 h of exposure to UV radiation was any degradation noted, and this degradation led to some loss in activity. Thus, while 2',3',22,23-tetrahydroazadirachtin was definitely more stable than were the other three compounds to UV-degradation, decreased chemical stability did not translate into decreased biological activity until 200 h of exposure to UV radiation. The chemical nature of the fully active degradation products of azadirachtin, 3-deacetylazadirachtin, and 22,23-tetrahydroazadirachtin, formed through exposure to UV radiation for up to 90 h, is unknown.

The claimed compositions have also been determined to function as antifeedants, as we have determined that isolated azadiractin does. To be effective as an antifeedant, a chemical should have a systemic mode of action. In other words, the chemical, when applied to the plant or on or about its roots, must be taken up by the plant so that as it grows it is distributed to protect new tissue as well as old. This prevents having to more frequently respray growing crops or to reapply the compositions to reach the roots of those crops. The claimed compositions are systemic.

It is anticipated that, for example, tetrahydroazadirachtin in the amount of 50 grams per acre in an acceptable carrier would be sufficient to enable it to function as both an insecticide and an as antifeedant. It is believed that the concentration of tetrahydroazadirachtin utilized for either function should be at least about 5 grams per acre. Of course, the claimed compositions may also be utilized to protect stored crops from foraging insects, and a lesser amount of these antifeedant and insecticidal compositions may be useful to protect such crops that may be, for example, maintained in bins or graineries.

The above experiments are to assist in understanding the invention and should not, of course, be construed as specifically limiting the invention. Such variations of the invention which would be within the purview of those in the art and all equivalents now known or later developed are to be considered to fall within the scope of the invention as hereinafter claimed.

We claim:

1. 2',3',22,23-tetrahydroazadirachtin.
2. The azadirachtin derivative product of the process of hydrogenation of azadirachtin over a hydrogenation catalyst using elevated pressure.
3. The azadirachtin derivative product of claim 2 wherein the process comprises:
   (a) isolating and substantially purifying azadirachtin from neem tree seeds or chinaberry tree seeds;
   (b) stirring said azadiractin in ethanol with the addition of hydrogenation under at least about 10 atmospheres of hydrogen;
   (c) filtration of the crude product of step (b); and
   (d) chromatographic purification of the product of step (c).
4. The azirdiractin derivative product of claim 3 wherein said chromatographic purification is accomplished using normal phase or reverse phase high pressure liquid chromatography.
5. The derivative of claim 2 wherein said derivative maintains substantially all insecticidal activity upon exposure to ultra-violet radiation for 400 hours.
6. The derivative of claim 3 wherein said derivative maintains substantially all insecticidal activity upon exposure to ultra-violet radiation for 400 hours.
7. A insecticidal composition comprising an insecticidally effective amount of the compound of claim 1 and an acceptable carrier.
8. A method for the control of insects comprising the application of a derivative product or composition of any of claim 1-5, 6 or 7 to an area where it is desired to control said insects.
9. The method of claim 8 wherein said application is accomplished by spraying.
10. The method of claim 8 wherein said application is accomplished by distributing said derivative product or said composition on or about the roots of growing plants.
11. A method for controlling insects comprising the compound of claim 1 applied in an amount of at least about 5 grams per acre.
12. The method of claim 11 wherein said compound is applied in an amount of about 50 grams per acre.

* * * * *